United States Patent
Beudeker

(10) Patent No.: US 7,566,466 B2
(45) Date of Patent: Jul. 28, 2009

(54) USE OF FOOD AND DRINK AS A DELIVERY SYSTEM FOR PHYTASE IN HUMANS

(75) Inventor: Robert Franciscus Beudeker, Hoorn (NL)

(73) Assignee: DSM IP Assets B.V., Heerlen (NL)

( * ) Notice: Subject to any disclaimer, the term of this patent is extended or adjusted under 35 U.S.C. 154(b) by 341 days.

(21) Appl. No.: 10/250,626

(22) PCT Filed: Jan. 9, 2002

(86) PCT No.: PCT/EP02/00438

§ 371 (c)(1), (2), (4) Date: Jul. 2, 2003

(87) PCT Pub. No.: WO02/054881

PCT Pub. Date: Jul. 18, 2002

(65) Prior Publication Data

US 2004/0058049 A1 Mar. 25, 2004

(30) Foreign Application Priority Data

Jan. 10, 2001 (EP) .................................. 01200069

(51) Int. Cl.
A23C 9/12 (2006.01)
(52) U.S. Cl. ................ 426/42; 426/52; 426/18; 426/56; 426/580; 426/590
(58) Field of Classification Search .......... 426/42, 426/52, 56, 18, 590, 580
See application file for complete search history.

(56) References Cited

U.S. PATENT DOCUMENTS

| 2,390,872 | A | * | 12/1945 | Dahlberg et al. | 426/522 |
|---|---|---|---|---|---|
| 5,667,990 | A | * | 9/1997 | Berka et al. | 435/69.1 |
| 5,853,779 | A | * | 12/1998 | Takebe et al. | 426/20 |
| 5,900,262 | A | * | 5/1999 | Iritani et al. | 426/53 |
| 6,033,897 | A | * | 3/2000 | Chu et al. | 435/245 |
| 6,039,942 | A | * | 3/2000 | Lassen et al. | 424/94.6 |
| 6,183,740 | B1 | * | 2/2001 | Short et al. | 424/94.6 |
| 6,284,502 | B1 | * | 9/2001 | Maenz et al. | 435/168 |
| 6,303,766 | B1 | * | 10/2001 | Grabau et al. | 536/23.1 |
| 6,638,562 | B1 | * | 10/2003 | Saitoh et al. | 426/654 |
| 6,699,704 | B1 | * | 3/2004 | van Loon et al. | 435/252.3 |
| 2002/0012985 | A1 | * | 1/2002 | Takebe et al. | 435/253.6 |

FOREIGN PATENT DOCUMENTS

| EP | 380343 | | 8/1990 |
|---|---|---|---|
| EP | 0682876 | * | 10/1998 |
| EP | 682876 | | 10/1998 |
| JP | 59166049 A | | 9/1984 |
| JP | 06-038745 | * | 2/1994 |
| JP | 07067635 A | | 3/1995 |
| JP | 2000-245340 | * | 9/2000 |
| WO | WO98/30681 | | 7/1998 |
| WO | 99/10473 | * | 3/1999 |
| WO | WO99/49740 | | 10/1999 |

OTHER PUBLICATIONS

Turk et al., Journal of Cereal Science 15(3):281-294 (1992).

* cited by examiner

*Primary Examiner*—C. Sayala
(74) *Attorney, Agent, or Firm*—Nixon & Vanderhye P.C.

(57) ABSTRACT

The present invention relates to the use of phytase to increase the uptake of minerals, and in particular calcium, in a diet for humans. Advantageously milk is used as the delivery system for phytase for human consumption.

24 Claims, No Drawings

USE OF FOOD AND DRINK AS A DELIVERY SYSTEM FOR PHYTASE IN HUMANS

CROSS-REFERENCE TO RELATED APPLICATION

This application is the national phase of PCT application PCT/EP02/00438 having an international filing date of 9 Jan. 2002, and claims priority from European application 01200069.1 filed 10 Jan. 2001. The contents of these documents are incorporated herein by reference.

FILED OF THE INVENTION

The present invention relates to the uptake of minerals such as calcium from food.

BACKGROUND OF THE INVENTION

Minerals such as Iron, Zinc and Calcium are important elements for human health. Iron deficiency results in anaemia which, in the case of pregnant women, is associated with significant increases in maternal mortality. Less severe anaemia results in a hampering of physical performance.

Iron needs in men and women have been assessed in terms of the amount of iron that must be absorbed to replace the body's losses and that needed to provide for normal body iron accretion rates during growth and pregnancy.

Zinc deficiency results in a depression in growth and severe skin lesions.

Calcium is very important in bone formation.

The availability of minerals such as Iron, Calcium and Zinc in animals and humans is hampered by the presence of compounds which form complexes with them. Phytic acid (inositol hexakisphosphate), for example, forms complexes with these minerals resulting in phytate salts. Phytates and phytic acid are found in virtually all plants and plant seeds. Phytic acid serves as a storage means for phosphorous source is plants.

Everyday foods such as bread, corn flakes and crackers contain considerable amounts of phytate and phytic acid. The consumption of such foods results in a reduced availability of minerals such as Iron, Zinc and Calcium.

SUMMARY OF THE INVENTION

Accordingly, the present invention provides a food or drink for human consumption, comprising a phytase.

The present invention further provides for:
the use of a phytase in a food or drink for increasing the availability of Calcium, Iron and/or Zinc of the food or drink for humans.
the use of a food or drink as delivery system for phytase for human consumption; and
the use of a phytase in the manufacture of a medicament for treating a mineral deficiency.

DETAILED DESCRIPTION OF THE INVENTION

The present invention provides foods and drinks comprising phytases, which are suitable for human consumption.

Typically, the foods and drinks of the invention will comprise phytase at a concentration of from 50 to 10,000 FTU/kg, preferably from 100 to 5,000 FTU/kg and most preferably from 500 to 1,500 FTU/kg.

Phytases are widespread in nature and have been found in bacteria, yeasts, fungi and plants and phytases from any of these may be used in the invention. The fungal enzyme Phytase from *Aspergillus niger* has been commercialized for use in animal feed and may also be used in the present invention. The gene encoding the enzyme has been cloned and the phytase enzyme has been overexpressed in *Aspergillus niger*. This fungus is grown on industrial scale in large fermentors allowing for the production of the enzyme. The fungus secretes considerable amounts of phytase which can be separated from the biomass in a series of filtration and ultrafiltration steps. The resulting concentrated ultrafiltrate is subsequently formulated into a stable granulate or liquid which may be used in the present invention. Inclusion of the enzyme in the diet results in liberation of phosphate from phytic acid and phytate during passage of the diet through the gastrointestinal tract of the animals.

The foodstuffs of the invention will typically be ones in which their preparation, storage or subsequent use do not involve conditions incompatible with phytase activity. The foods may be ones rich in phytic acid or phytates such as bread, cakes, pastries, breakfast cereals or crackers. The foods may also be enriched in minerals, in particular in Calcium, Zinc, and/or Iron and especially in Calcium. In a preferred embodiment the foods will be ones whose preparation do not involve heat treatments above 100° C. and/or which are kept chilled prior to use.

We have found beneficial effects of phytase on the availability of Calcium, Iron and Zinc in humans when taken together with food containing these elements. The present invention describes a method to deliver the enzyme in a safe and attractive way to humans.

One way to deliver the phytase to humans is the uptake around or together with a meal, for example, pills which could be taken around eating time. However, since people like to reduce the number of pills they take to the minimum and since there is a chance of forgetting to take these pills. The preferred method of delivering the phytase is in the food or drink of a subject by adding the phytase to the food or drink. Hence another way to increase the availability of the essential elements comprises the processing of food with phytase to decrease the phytate content of the diet. Although, the invention provides for foods comprising phytases for some foods this may involve too large an effort from the food processing companies or would not work since the conditions under which the food is processed are incompatible with the conditions under which the enzyme would show activity. Accordingly, in a preferred embodiment the invention provides for drinks comprising a phytase.

The drink is typically tailored for human consumption in terms of taste and looks. The drink is preferably a flavoured drink and may be carbonated. Typically the drink is one which is kept chilled or refrigerated. The drink may be Calcium enriched.

The preferred way to deliver phytase to humans would be milk, preferably pasteurized cow's milk, since this is consumed every day by many people, is stored cool and contains a lot of Calcium. Alternatively goat or sheep milk may be used. Milk is frequently fortified with extra Calcium. This is practically useless if the milk is consumed simultaneously with bread or corn flakes containing high amounts of phytic acid or phytate since virtually all Calcium ions would be made unavailable due to the formation of Calcium phytate complexes. However, when a phytase is added this helps ensure the consumers derives full benefit from the additional calcium. The principle behind the present invention is believed to be the beneficial effects of the enzyme phytase on the availability of minerals such as Iron, Zinc and Calcium for uptake from food. Phytate and Phytic acid may be converted into inositol and inositol phosphates by the enzyme Phytase (for example, 3-phytase EC 3.1.3.8, 6-Phytase EC 3.1.3.8 or 3,6-Phytase EC 3.1.3.8 either of which may be employed in the invention). In this way the formation of complexes such as Calcium phytate complex can be substantially reduced and therefore the minerals, in this example Calcium, is better available for uptake during consumption of food.

Milk is heat-treated to kill micro-organisms and to destroy undesirable enzyme activities. This heat treatment, termed pasteurization, is carried out at 60–85° C. during a short period of up to 20 seconds. These temperatures in a watery environment are such that it would be expected that all phytase enzyme activity would be destroyed.

However, surprisingly we found that a large proportion of added phytase activity appears to be resistant to this heat treatment, whereas similar treatments in water result in a marked reduction in phytase activity. Milk represents a suitable means for delivering this enzyme to humans using milk as a functional food enriched with minerals and phytase.

The present invention also provides foods comprising or made with a milk of the invention such as cheeses, yoghurts, milk shakes, creams and desserts.

Although the milks of the invention are typically pasteurized the invention also provides unpasteurized milks comprising a phytase, as well as UHT milks comprising a phytase. The phytase may be added to the milk before, after or during pasteurization but preferably prior to pasteurization. If the phytase is added post pasteurization it is preferably added in a sterile form.

The food and drinks of the invention are typically suitable for human consumption in terms of their taste and appearance. They will be typically given to healthy individuals, usually as part of their normal diet. However, the food and drinks of the invention may be given to those suffering or at risk of mineral deficiency and may be given to treat, alleviate or prevent such deficiencies. They may be given to individuals suffering from anemia, calcium, zinc and/or iron deficiency. They may also be given as part of the normal diet of pregnant women or women recently having given birth. They may be given to men and women intending to conceive.

By Phytase is intended an enzyme that is capable of liberating at least one phosphate group from phytate.

The examples herein are give by way of illustration and are in no way intended to limit the scope of present invention. It will be obvious to those skilled in the art that phytase preparations used in this application may be obtained from various sources (of bacterial, fungal or plant origin).

EXAMPLES

Example 1

Application of Phytase in Milk Prior to Pasteurization

Various phytase preparations are commercially available. We have taken NATUPHOS™ 5000 G (DSM, Delft, The Netherlands) and the corresponding liquid formulation NATUPHOS™ L as well as the original concentrated ultrafiltrate as test substances.

We have compared the results of pasteurization during 20 seconds in cow's milk with those in water on phytase activity. Results, expressed as FTU/kg are shown in Table 1.

Phytase units were added to milk and water to a final concentration of 1000 FTU/kg. One phytase unit is defined as the amount of enzymes which liberates one micromole of phosphate per minute from 1 mM Na-phytate at pH 5.5 at 37° C. The analytical method has been published (Engelen, van Ransdorp en Smit, J.A.O.C. Int. 77:760–764 (1994)).

TABLE 1

| Phytase stability on milk and water | | | |
|---|---|---|---|
| Treatment | | | |
| Milk 60° C. FTU/kg | Milk 85° C. FTU/kg | Water 60° C. FTU/kg | Water 85° C. FTU/kg |
| NATUPHOS ™ 5000 G | 995 | 925 | 553 | 275 |
| NATUPHOS ™ 5000 L | 989 | 931 | 547 | 284 |
| Phytase ultrafiltrate | 997 | 936 | 549 | 263 |

The invention claimed is:

1. A drink for human consumption which comprises an isolated phytase and milk, wherein said milk is selected from the group consisting of cow's milk, goat's milk, and sheep's milk.

2. The drink according to claim 1, wherein the isolated phytase content is 50–10,000 FTU/kg drink.

3. The drink according to claim 1, wherein the isolated phytase is of microbial origin.

4. The drink according to claim 3, wherein the isolated phytase is from *Aspergilllus*.

5. The drink according to claim 1, wherein said milk is cow's milk.

6. A method to increase availability of calcium in a drink that comprises milk which comprises
adding an amount of isolated phytase effective to provide said increase to a milk-containing drink, wherein said milk is selected from the group consisting of cow's milk, goat's milk, and sheep's milk; and
pasteurizing said isolated phytase-containing drink.

7. A method to deliver isolated phytase to a human which comprises providing the drink of claim 1 to the human.

8. The drink according to claim 2, wherein the isolated phytase content is 100–5,000 FTU/kg drink.

9. The drink according to claim 8, wherein the isolated phytase content is 500–1,500 FTU/kg drink.

10. The method of claim 6, wherein said milk is cow's milk.

11. The method of claim 6, wherein said milk is pasteurized milk.

12. The method of claim 6, wherein the isolated phytase is of microbial origin.

13. The drink according to claim 1 which is pasteurized.

14. The method of claim 12, wherein the isolated phytase is from *Aspergillus*.

15. The method of claim 6, wherein the isolated phytase content is 50–10,000 FTU/kg drink.

16. The method of claim 15, wherein the isolated phytase content is 100–5,000 FTU/kg drink.

17. The method of claim 16, wherein the isolated phytase content is 500–1,500 FTU/kg drink.

18. A method to increase availability of calcium in a drink that comprises milk which comprises
adding an amount of isolated phytase effective to provide said increase in sterile form to pasteurized milk, wherein said milk is selected from the group consisting of cow's milk, goat's milk, and sheep's milk.

19. The method of claim 18, wherein said milk is cow's milk.

20. A method to deliver isolated phytase to a human which comprises providing the drink of claim 10 to the human.

21. A drink for human consumption which consists of an isolated phytase and milk, wherein said drink is pasteurized and said milk is selected from the group consisting of cow's milk, goat's milk, and sheep's milk.

22. The drink according to claim 21, wherein the isolated phytase is from *Aspergilllus*.

23. The drink according to claim 21, wherein said milk is cow's milk.

24. A method to deliver isolated phytase to a human which comprises providing the drink of claim 21 to the human.

* * * * *